United States Patent
Hallset (10) Patent No.: US 9,689,787 B2
(45) Date of Patent: Jun. 27, 2017

(54) TECHNICAL SYSTEM, METHOD AND USE FOR ONLINE MEASURING AND MONITORING OF THE PARTICLE CONTENTS IN A FLOW OF INJECTION WATER IN AN UNDERWATER LINE

(75) Inventor: Jan Olav Hallset, Hafrsfjord (NO)

(73) Assignee: SEABOX AS, Sandnes (NO)

( * ) Notice: Subject to any disclaimer, the term of this patent is extended or adjusted under 35 U.S.C. 154(b) by 242 days.

(21) Appl. No.: 13/880,912

(22) PCT Filed: Oct. 20, 2011

(86) PCT No.: PCT/NO2011/000295
§ 371 (c)(1),
(2), (4) Date: Apr. 22, 2013

(87) PCT Pub. No.: WO2012/053898
PCT Pub. Date: Apr. 26, 2012

(65) Prior Publication Data
US 2013/0258092 A1 Oct. 3, 2013

(30) Foreign Application Priority Data
Oct. 22, 2010 (NO) .................................. 20101490

(51) Int. Cl.
*H04N 7/18* (2006.01)
*G01N 15/14* (2006.01)
*B08B 9/032* (2006.01)

(52) U.S. Cl.
CPC ........... *G01N 15/14* (2013.01); *B08B 9/0321* (2013.01); *G01N 15/1463* (2013.01); *G01N 2015/1497* (2013.01); *H04N 7/18* (2013.01)

(58) Field of Classification Search
CPC ...... H04N 5/2252; H04N 7/183; H04N 7/185; G01N 15/14; G01N 15/1463; G01N 2015/1497; B08B 9/0321
(Continued)

(56) References Cited

U.S. PATENT DOCUMENTS 4,075,462 A 2/1978 Rowe
4,283,128 A 8/1981 Meyer et al.
(Continued)

FOREIGN PATENT DOCUMENTS

GB 2386625 A 9/2003
WO 2004/090284 A1 10/2001
(Continued)

OTHER PUBLICATIONS

International Preliminary Report on Patentability issued in connection with PCT/NO2011/000295.
(Continued)

*Primary Examiner* — Michael Lee
(74) *Attorney, Agent, or Firm* — Conley Rose, P.C.

(57) ABSTRACT

Technical system and method for online measuring and monitoring of the particle content in an injection water flow (6') in an underwater line (8). The system comprises a data gathering means, a data communication link (48) and a data receiving means comprising an image analysis apparatus (2) provided with: a water sample line (18) for throughput of a partial flow (6") of the injection water flow (6'); a means of conveyance (24) connected to the water sample line (18) for transport of the partial flow (6"); a light-transparent flow portion (18') disposed along the water sample line (18); a camera (26) at the flow portion (18'); at least one light source (30, 32) for emission of light (34) via the flow portion (18') and into the camera (26); an electronic control means (36) for (a) control of the image recording of the camera (26); (b) reception of image material from the camera (26); and (c) transmission of the image material to the data receiving means; and at least one energy supply. The image analysis apparatus (2) is disposed in a water-tight housing (4) under water (6); wherein the water sample line (18) is connected to the underwater line (8) at a connection site (62) between
(Continued)

a shipment site (50: 64) for the injection water (6') and an injection well (56); wherein the data receiving means is located at a distance from the image analysis apparatus (2); and wherein the control means (36) of the image analysis apparatus (2) is connected to the remote data receiving means.

19 Claims, 4 Drawing Sheets

(58) Field of Classification Search
USPC .......................................................... 348/81
See application file for complete search history.

(56) References Cited

U.S. PATENT DOCUMENTS

| 4,783,599 | A | 11/1988 | Borden |
|---|---|---|---|
| 6,184,978 | B1 | 2/2001 | Kasdan et al. |
| 6,888,631 | B2 | 5/2005 | Eriksson |
| 7,162,057 | B1 | 1/2007 | Roth et al. |
| 7,604,051 | B2 | 10/2009 | Pinchin |
| 2006/0060543 | A1 | 3/2006 | Appleford et al. |
| 2007/0035736 | A1* | 2/2007 | Vannuffelen ............ E21B 49/08 356/432 |
| 2009/0294123 | A1 | 12/2009 | Mescall et al. |
| 2010/0005866 | A1* | 1/2010 | Sebok et al. .................. 73/54.43 |
| 2010/0059221 | A1 | 3/2010 | Vannuffelen et al. |
| 2011/0040501 | A1 | 2/2011 | Martin et al. |

FOREIGN PATENT DOCUMENTS

| WO | WO 2007035106 A1 * | 3/2007 |
|---|---|---|
| WO | 2007/073198 A1 | 6/2007 |

OTHER PUBLICATIONS

Response to Written Opinion filed in connection with PCT/NO2011/000295.

International Search Report issued in connection with PCT/NO2011/000295.

* cited by examiner

TECHNICAL SYSTEM, METHOD AND USE FOR ONLINE MEASURING AND MONITORING OF THE PARTICLE CONTENTS IN A FLOW OF INJECTION WATER IN AN UNDERWATER LINE

This application is a national phase of PCT/NO2011/000295, filed Oct. 20, 2011, and claims priority to NO 20101490, filed Oct. 22, 2010, the entire contents of both of which are hereby incorporated by reference.

FIELD OF THE INVENTION

The invention concerns a technical system and a method for online measuring and monitoring of the particle content in an injection water flow in an underwater line. The invention also comprises use of the technical system and the method.

The particle content in the injection water flow may comprise particles of an inorganic and/or organic origin, of different sizes and/or shapes, and of varying amounts and/or distributions.

BACKGROUND OF THE INVENTION

The background of the invention relates to a need in the industry for a more or less continuous, and at least a regular, measuring, monitoring and verification of the particle content in an injection water flow in an underwater line. As such, there is a need for a technical solution rendering possible to measure, monitor and verify potential changes in the particle content in the injection water flow over time, but also potential abrupt changes.

In context of water injection into a well, it is common to filter and treat the raw water of the injection water at a shipment site for the injection water before the finally treated injection water is transported onwards to a receiving site for the injection water. The water treatment is carried out in order to obtain a water quality acceptable to the water injection operation of interest. The most elementary water treatment consists in removing inorganic and/or organic solid particles from the raw water through filtering and/or sedimentation (which is more uncommon) of undesirable particles from the raw water. It is also common to treat the raw water chemically at the shipment site. Typically, this shipment site is comprised of a surface installation offshore, for example a bottom-fixed platform or a floating installation, whereas the receiving site is comprised of an injection well and/or a subterranean reservoir, for example an oil reservoir, to which the well is connected in a flow-communicating manner. Such water injection is usually carried out in a subsea well, but it may also be of interest to transport the injection water from the shipment site and further onto a land-based injection well. In both situations, long transport distances may be involved between the shipment site and the receiving site for the injection water.

For such water injection it is customary to take the raw water from a body of water located in vicinity of the shipment site. Thus, the body of water may, for example, be comprised of seawater, or of water from a lake, river, spring or a groundwater occurrence. This raw water may contain inorganic and/or organic particles of different sizes and/or shapes, and of varying amounts and/or distributions. Moreover, the raw water is generally taken from a surface layer of the body of water. However, the water quality in such a surface layer may vary a lot due to weather-dependent and/or seasonal influences. Thus, the particle content in the surface layer may fluctuate due to variations in the temperature, salt content and sediment content of the water, but also due to the current conditions and/or biological activity in the raw water. Typically, such a particle content comprises particles in the form of inorganic weathering products, for example sand-, silt- and/or clay particles, but also organic particles, for example aquatic organisms, including plankton, various bacteria, including anaerobic and sulphate-reducing bacteria capable of generating hydrogen sulphide gas ($H_2S$), and also bacterial film residues and similar.

Besides creating relatively unstable operating conditions and also occasional problematic operating conditions at the shipment site, especially for installations offshore, such fluctuations in the particle content of the raw water may also influence the particle content in, and hence the quality of, the injection water being transported away from the shipment site. This is customary even if the water has been treated, for example filtered, at the shipment site.

If the raw water for the injection water comprises produced water from a separation plant for hydrocarbon fluid, for example crude oil, also the produced water may have a undesirable organic and/or inorganic particle content, including sand-, silt- and/or clay particles, and also various bacteria, bacterial film residues, oil droplets, gas bubbles, etc. Also variations in the particle content of the produced water may influence the quality of the injection water being transported away from the shipment site.

Furthermore, the injection water may contain various corrosion products, for example rust particles, and/or various depositional products, so-called "scale", from the shipment site and/or the underwater line. Also this may influence the quality of the injection water.

If such undesirable particles are not adequately removed from the injection water, the particles may cause large problems in the underwater line, the injection well and/or in an oil-bearing reservoir to which the well is connected in a flow-communicating manner. Thus, serious corrosion and/or organic fouling may arise in the underwater line and/or in the well. So-called reservoir souring may also arise if the injection water carries along anaerobic bacteria into a subterranean oil reservoir. Moreover, particularly fine-grained solid particles in the injection water may cause reduced permeability in the oil reservoir. This may inhibit the ability of a water-flood front to flow through the reservoir in order to force more crude oil out of the reservoir. By so doing, the efficiency of water injection as a means of achieving increased recovery from the oil reservoir is also restricted.

If possible to carry out online measuring and monitoring of the particle content in the injection water flow in the underwater line, potential changes in the particle content may be detected quickly. Such changes in the particle content may indicate unacceptable conditions at the shipment site and/or may indicate or cause unacceptable conditions in the underwater line and/or at the receiving site. By so doing, it will also be possible, if required or desirable, to measure and monitor the particle content in the injection water flow at several sites along the underwater line. This may be of interest during transport of injection water over large distances, for example from a shipment site offshore and onto a land-based injection well. On the basis of such online measuring and monitoring, it will also be possible to quickly initiate actions that may remedy the negative development at the shipment site, in the underwater line and/or at the receiving site.

Prior Art and Disadvantages Thereof

According to prior art, measuring and monitoring of the particle content of the injection water is carried out on a surface installation, for example a bottom-fixed or floating platform offshore. This is typically carried out via laboratory analyses of samples of finally treated injection water, i.e. after filtration of the raw water. On such surface installations, a number of methods are used to measure and possibly characterize the particle content in the injection water.

A common method consists in sieving or sedimenting particles from samples of the finally treated injection water, i.e. after filtration of the raw water, whereupon laboratory analyses of the particles separated from the injection water are carried out. Manual microscopy is also used to count the number of particles present in a liquid sample. Obviously, these methods are unpractical and unsatisfactory if online measuring and monitoring of the particle content in an injection water flow is desired.

Another method comprises use of a so-called electric sensing zone (ESZ) in order to analyse and characterize various particle sizes in a liquid. In this context, a so-called Coulter counter is used, which is an apparatus for counting particles and measuring particle sizes in a liquid. The apparatus measures electric capacitance values in an electrified liquid passing through a small measuring aperture, i.e. sensing zone, in the apparatus. By so doing, information about the distribution of particle sizes in the liquid may be provided. The apparatus is strongly dependent on correct calibration of said measuring aperture. The apparatus is not suitable for handling a wide spectrum of particle sizes in the liquid, which passes the measuring aperture of the apparatus, without having to change the magnitude of the measuring aperture.

Ultrasonic sensors are also used for measuring larger particles. Such sensors, however, are not suitable for measuring the smaller particle sizes generating, typically, most problems in context of water injection.

On surface installations, it is also customary to use apparatuses based on laser diffraction for measuring particle distribution in a liquid. The particle distribution, however, is not measured directly in such apparatuses. In context of laser diffraction, particles being illuminated by the laser will appear as scatter points for the laser light. The resulting scatter pattern is represented in the form of electronic measuring values, which then are used in one or more algorithms to determine the distribution of particle sizes in the liquid. This method is based on assumptions with respect to the properties of the different types of particle materials that may occur in the liquid. The method is therefore sensitive to erroneous assumptions with respect to the properties of the types of particle materials that may occur in the liquid.

On surface installations, it is also customary to use so-called image analysis as a technique for measuring and monitoring the particle content in produced water from a separation plant for produced crude oil. In this context, a camera is used, typically a so-called CCD-camera ("charged-coupled device"-camera) with a microscope lens, for image recording of a particle-laden water flow of the produced water. This water flow is illuminated by a light source in order to detect the particle content in the produced water. In this context, it is most common to send light through the water flow from an opposite light source, which typically is comprised of a so-called LED-light source ("light-emitting diode"-light source). The image recording and processing of the image material is controlled electronically via an associated data program. By using such image analysis techniques, it is possible to measure different physical properties of each particle in the produced water, but also to measure the distribution of different types, amounts and/or sizes of particles in the water. Via such image analysis, it is possible, among other things, to determine the shape, size, geometric centre of gravity, optical density, etc. for each particle in the water. Via electronic processing of the image material, it is also possible to combine several physical properties (or parameters) of each particle, thereby allowing the particle to be characterized better. By so doing, the different particles in the water may be classified with respect to e.g. material type, shape, size, amount, distribution, etc. Thus, such an image analysis may determine, for example, whether a particle is an oil droplet, a gas bubble, a sand grain or an organic particle, for example a bacterial cell or a residue of a bacterial film. Such an image analysis technique may also determine the distribution of amounts of the different particles in the produced water. This image analysis technique is therefore well suited for online measuring and monitoring of the particle content in the produced water.

WO 00/46586 (which corresponds to U.S. Pat. No. 7,162,057) describes an apparatus which makes use of such an image analysis technique, the apparatus of which is structured for monitoring the particle content in a liquid.

U.S. Pat. No. 4,075,462, U.S. Pat. No. 4,283,128 and WO 97/43638 (which corresponds to U.S. Pat. No. 6,184,978) also describe apparatuses and methods for measuring the particle content in a flow of liquid.

Objects of the Invention

The primary object of the invention is to be able to carry out online measuring and monitoring of the particle content in an injection water flow in an underwater line.

Another object is to be able to carry out such measuring of the particle content at several different sites along the underwater line.

A further object is to be able to carry out such measuring of the particle content in a position located in the immediate vicinity of the injection well. By so doing, the particle content may be measured immediately before pumping the injection water down into the injection well and out into a subterranean reservoir.

General Description of how the Objects are Achieved

The objects are achieved by virtue of features disclosed in the following description and in the subsequent claims.

According to a first aspect of the invention, a technical system for online measuring and monitoring of the particle content in an injection water flow in an underwater line is provided, wherein the technical system comprises a data gathering means, a data communication link and a data receiving means, and wherein the data gathering means comprises an image analysis apparatus provided with the following components:

- at least one water sample line provided with an inlet and an outlet for throughput of a partial flow of the injection water flow;
- at least one means of conveyance connected, in a flow-communicating manner, to the water sample line for transport of said partial flow;
- at least one light-transparent flow portion disposed along the water sample line;
- at least one camera for recording image material of the particle content in the partial flow, wherein the camera is disposed at a first side of the light-transparent flow portion;

at least one light source for emission of light via the light-transparent flow portion and into the camera;

at least one electronic control means structured for (a) control of the image recording of the camera; (b) reception of image material from the camera; and (c) transmission of this image material to said data receiving means, which is a receiving site for the image material; and at least one energy supply for operation of said means of conveyance, light source, camera and electronic control means.

The distinctive characteristic of the technical system is that the image analysis apparatus is disposed in a water-tight housing placed under water;

wherein the inlet and the outlet of the water sample line is connected, in a flow-communicating manner, to the underwater line at a connection site located between a shipment site for the injection water and an injection well;

wherein said data receiving means is located at a distance from the image analysis apparatus; and wherein the electronic control means of the image analysis apparatus is connected to the remote data receiving means. Thereby, image material being transmitted from the image analysis apparatus may be monitored online at a remote site.

By means of the present technical system, it is possible to carry out online measuring, monitoring and verification of the particle content in the injection water flow in the underwater line. On the other hand, none of the above-mentioned patent publications WO 00/46586, U.S. Pat. No. 4,075,462, U.S. Pat. No. 4,283,128 or WO 97/43638 describe apparatuses and/or methods for online measuring of particles under water in context of water injection in a well.

By means of this technical system, which is based on image analysis techniques, it is possible to measure different physical properties of each particle in the injection water. It is also possible to measure the distribution of different types, amounts and/or sizes of particles in the injection water. Via image analysis it is possible, among other things, to determine the shape, size, geometric centre of gravity, optical density, etc. for each particle in the water. Via electronic processing of the image material, it is also possible to combine several physical properties (or parameters) of each particle, thereby allowing the particle to be characterized better. By so doing, the different particles in the injection water may be classified with respect to e.g. material type, shape, size, amount, distribution, etc. Such an image analysis may determine, for example, whether a particle is a sand grain, a rust particle, a scale particle or an organic particle, for example a bacterial cell or a residue of a bacterial film, an oil droplet or a gas bubble. This image analysis technique may also determine the distribution of amounts of the different particles in the injection water.

If, by means of the present technical system, sudden or progressive changes are detected in the particle content of the injection water flow, and these changes indicate unacceptable conditions at the shipment site and/or cause or indicate unacceptable conditions in the underwater line and/or at the receiving site, actions remedying the negative development at the shipment site, in the underwater line and/or at the receiving site may be initiated. For example, a temporary shut-down of the water injection may be initiated if the particle content in the raw water for the injection water increases significantly due to sudden weather-dependent and/or seasonal influences, for example due to storm activity. On the other side, progressive changes in the particle content in the injection water flow downstream of the shipment site for the injection water may indicate increasing rust formation, scaling and/or biofilm formation in the underwater line. Advantageously, during such progressive changes, the particle content in the injection water flow may be measured at several sites along the underwater line, thereby allowing for a better determination of the location of the negative development in the underwater line.

This underwater line may be comprised of a pipeline, a hose or similar.

Said data receiving means in the present technical system may comprise various electronic components and equipment structured for reception, display and verification of image data received online from the electronic control means of the image analysis apparatus. By so doing, the data receiving means may also be structured in a manner allowing it to produce one or more alarm signals if unacceptable conditions are detected in the particle content in the injection water in the underwater line and/or at the receiving site.

Further, said means of conveyance in the image analysis apparatus may comprise a suitable pumping means.

The means of conveyance, for example a pump, may also be structured in a manner allowing it to reverse the flow direction of the partial flow through the water sample line for cleaning of the water sample line. Such a reverse flow may contribute to disengage and remove a particle blockage in the water sample line.

As an alternative or addition, the water sample line may be associated with an ultrasonic treatment apparatus or sonicator for cleaning of the water sample line. Such an apparatus uses high-frequency sound waves to disengage particles fixed to the inside of the water sample line.

Further, said camera in the image analysis apparatus may comprise a microscope lens. This may be required for allowing the smallest particle sizes in the water sample line to be measured.

Advantageously, the at least one camera may comprise a CCD-camera ("charged-coupled device"-camera). Such a camera is suitable for digital image recording and for recording high quality images.

Further, the at least one light source in the image analysis apparatus may comprise so-called LED-lighting ("light-emitting diode"-lighting). Such light-emitting diodes have a long life and use little power and are therefore well-suited for placement in inaccessible places, such as under water. Besides, said light source may also comprise invisible lighting, such as infrared and ultraviolet lighting, should this be appropriate in the image analysis apparatus of interest.

Further, the at least one light source may comprise at least one light source disposed at the same side as the camera, for example in the camera, for emission of light for recording, in the camera, of reflected light from image material of the particle content in the partial flow. For example, this may concern emission of ultraviolet light being reflected by particles, for example oil droplets, in the partial flow.

As an alternative or addition, the at least one light source may comprise at least one light source disposed at a second side, opposite said first side, of the light-transparent flow portion of the water sample line for emission of light therethrough and into the camera for recording image material of the particle content in the partial flow. Generally, such a light transmitting arrangement will be required for measuring small, and usually the very smallest, particles in the partial flow. This will also be required for measuring optical density for more or less transparent particles, for example various organic particles/organisms.

Further, and as an alternative or addition, said electronic control means in the image analysis apparatus may also be structured for processing of image material from the camera. By so doing, raw particle image data being registered by the camera may be processed electronically via a suitable data program associated with the electronic control means. Thereby, the image material being transmitted to said remote data receiving means will be processed, fully or partially, and hence will be finally treated, fully or partially, for online monitoring and verification of the particle content of the injection water flow.

As a further alternative or addition, said remote data receiving means may be structured for processing of image material from the camera. By so doing, raw particle image data being registered by the camera may be transmitted, fully or partially, to the remote data receiving means for further processing therein. With today's technical solutions, such a flow of data most likely will require fibre-optical data transmission for obtaining a sufficiently large data transmission capacity.

Yet further, said at least one energy supply may comprise at least one battery associated with the image analysis apparatus for operation of said means of conveyance, light source, camera and electronic control means.

As an alternative or addition, the at least one energy supply may comprise at least one energy source located at a distance from the image analysis apparatus, the energy source of which is cable-connected to the image analysis apparatus for transmission of working power thereto.

Moreover, the image analysis apparatus may be provided with at least two water sample lines, including at least one primary water sample line and at least one secondary (reserve) water sample line, wherein each of the at least two water sample lines is provided with its own camera, and wherein the image analysis apparatus is provided with a valve means for selective control of the partial flow into a selected water sample line. The selective control may be carried out via remote control of the valve means, for example via the electronic control means of the image analysis apparatus, or via a direct connection to the valve means. If a primary water sample line should become blocked by particles, the partial flow may be redirected, by means of the valve means, to a secondary (reserve) water sample line. The image analysis apparatus may possibly comprise several such secondary water sample lines.

As an alternative or addition, the image analysis apparatus may also be provided with at least two primary water sample lines; wherein each of the at least two, primary water sample lines is provided with its own camera. By so doing, it is possible to structure each camera with an associated electronic control means for reception, transmission and potential processing of image material taken from certain types and/or size ranges of particles in each primary water sample line. In this context, each camera may be associated with its own electronic control means. Alternatively, a common electronic control means may be used.

Further, said connection site for the image analysis apparatus may be located in vicinity of the injection well, for example within 500 m of the injection well. This renders possible to carry out online measuring, monitoring and verification of the particle content of the injection water flow immediately before pumping the injection water down into the injection well. In this context, the connection site may be comprised of a wellhead for the injection well. By so doing, the image analysis apparatus may be connected to, or integrated in, the wellhead.

Yet further, said shipment site for the injection water may comprise a surface installation. In this context, the surface installation may be located offshore, for example in the form of a bottom-fixed platform, a floating installation or a floating vessel.

As an alternative or addition, the injection water from the surface installation may comprise produced water from a separation plant for hydrocarbon fluid, for example crude oil, connected to the surface installation.

As a further alternative or addition, the injection water from the surface installation may comprise water taken from a body of water within which the underwater line is located. Thus, the water from the body of water may be comprised of seawater, for example high-salinity seawater, and/or of water taken from a lake, river or similar.

Further, the remote data receiving means of the technical system may be located on said surface installation. Thereby, it is possible to carry out online measuring, monitoring and verification of the particle content of the injection water flow at the shipment site for the injection water. This is very practical with respect to being able to quickly initiate remedial actions should the particle content of the injection water flow exhibit a negative development.

As an alternative or addition, said shipment site for the injection water may comprise at least one underwater installation for treatment of the injection water.

Advantageously, the underwater installation may be placed on or immediately above a seabed, river bottom or bottom of a lake.

In this context, the injection water may comprise produced water from a separation plant for hydrocarbon fluid, for example crude oil, disposed under water and connected to said underwater installation. The applicant has been informed that such an underwater separation plant has been supplied for use in the Norwegian sector of the North Sea.

As an alternative or addition, the injection water may comprise water taken from a body of water within which the underwater installation is located. Thus, the water from the body of water may be comprised of seawater, for example high-salinity seawater, and/or of water taken from a lake, river or similar.

Yet further, the at least one underwater installation for treatment of the injection water may comprise at least one device for filtering and removal of solid particles from the injection water, which in this context may be comprised of raw water. Such filtering may comprise conventional dead-end filtration of the injection water. In addition, or as an alternative, such filtering may comprise so-called cross-flow filtration, also denoted as tangential flow filtration, of the injection water.

As an alternative or addition, the at least one underwater installation may comprise at least one device for removal, without filtration, of solid particles from the injection water, which also in this context may be comprised of raw water. An example of such an underwater device is described in WO 2007/035106 A1. This underwater device comprises a closed space structured so as to allow the injection water to be led directly into a lower portion of the closed space, the space of which is also structured so as to allow treated water to be led out of an upper portion of the closed space. This closed space also has a cross-sectional area structured so as to allow the water to flow from the lower portion to the upper portion at a flow velocity being sufficiently low for undesirable solid particles to precipitate from the water by means of gravitation, so-called sedimentation. Further, this closed space may be formed as a receptacle or module being placed on, for example, a seabed or similar.

Further, and as an alternative or addition, the at least one underwater installation may comprise at least one device for chemical treatment of the injection water. Preferably, such a chemical treatment device will be placed downstream of the above-mentioned devices for filtering and/or sedimentation of solid particles. An example of such a chemical treatment device is described in WO 2004/090284 A1. This patent publication concerns a method and an apparatus for underwater chemical treatment of injection water, wherein a module-based underwater apparatus, which is connected to an injection well for injection of the water, is used. The apparatus contains at least one receptacle provided with at least one type of water-soluble solid-state chemical. The receptacle may, for example, be replaced by means of a remote-controlled underwater vehicle ("ROV"). Thereafter, the water is brought into contact with the solid-state chemical, whereby it is gradually dissolved and mixed with the water. The finally treated water is then injected into a reservoir associated with the well. By so doing, chemical treatment and water injection may be carried out without having to use an immediately overlying surface installation or -vessel. The water-soluble solid-state chemical may comprise chlorine and/or biocide, but also various other chemicals, such as said oxygen scavengers, corrosion inhibitors and scale inhibitors. This chemical treatment device may be comprised of a separate unit or be incorporated in the above-mentioned underwater device for removal, without filtration, of undesirable solid particles from the injection water.

As a further alternative or addition, the at least one underwater installation may comprise at least one device for destruction of organic material in the injection water. An example of such a destruction device is described in WO 2007/073198 A1. This patent publication concerns a method and a device for destructing organic material in injection water for an injection well. The device makes use of at least one electrochemical cell with associated operating means for in situ electrolytic generation, from water, of at least short-lived, free hydroxyl radicals. By means of the operating means, the electrochemical cell is structured in a manner allowing it to conduct the injection water therethrough as a source material for in situ generation of at least said free hydroxyl radicals from the injection water. Such free hydroxyl radicals will immediately destruct organic material engaged in the injection water. This destruction device may be comprised of a separate unit or be incorporated in the above-mentioned underwater device for removal, without filtration, of undesirable solid particles from the injection water. As a further alternative, the destruction device may be assembled together with the above-mentioned chemical treatment device.

For a shipment site comprising at least one such underwater installation for treatment of the injection water, said remote data receiving means may be located on a surface installation, for example on a bottom-fixed platform, a floating installation or on a floating vessel. Alternatively, the remote data receiving means may be located onshore, for example in a building within which an operator of said underwater installation is located. If online monitoring on such a remote site exhibits a negative development in the particle content of the injection water flow, it is possible, in both cases, to initiate remedial actions, via remote control, in the at least one underwater installation for treatment of the injection water. For example, a remote-controlled and temporary shut-down of the water injection may be initiated if said particle content increases significantly due to sudden weather-dependent and/or seasonal influences, for example due to storm activity and current activity in the water surrounding the underwater installation.

Further, said data communication link between the data gathering means and the data receiving means may comprise a cabled connection, for example a so-called umbilical, wherein the cabled connection may comprise various lines, including electric wires and fibre-optical cables, for transmission of image material from the at least one camera in the present image analysis apparatus. Such a cabled connection may also comprise one or more lines for transmission of energy to the means of conveyance, light source, camera and electronic control means of the image analysis apparatus.

As an alternative or addition, said data communication link may comprise a wireless connection, for example a radio frequency connection and/or an acoustic connection, for transmission of image material from the at least one camera in the present image analysis apparatus.

According to a second aspect of the invention, a method for online measuring and monitoring of the particle content in an injection water flow in an underwater line is provided, wherein the method makes use of a technical system comprising a data gathering means, a data communication link and a data receiving means, and wherein the data gathering means comprises an image analysis apparatus provided with the following components:
- at least one water sample line provided with an inlet and an outlet;
- at least one means of conveyance connected, in a flow-communicating manner, to the water sample line;
- at least one light-transparent flow portion disposed along the water sample line;
- at least one camera disposed at a side of the light-transparent flow portion;
- at least one light source disposed at the light-transparent flow portion of the water sample line;
- at least one electronic control means structured for (a) control of the image recording of the camera; (b) reception of image material from the camera; and (c) transmission of this image material to said data receiving means, which is a receiving site for the image material; and
- at least one energy supply for operation of said means of conveyance, light source, camera and electronic control means.

The distinctive characteristic of the method is that it comprises the following steps:
(A) disposing the image analysis apparatus in a water-tight housing and placing the housing under water;
(B) connecting, in a flow-communicating manner, the inlet and the outlet of the water sample line to the underwater line at a connection site located between a shipment site for the injection water and an injection well;
(C) connecting, by means of said data communication link, the image analysis apparatus to a data receiving means located at a distance from the image analysis apparatus;
(D) transporting, by means of said means of conveyance, a partial flow of the injection water flow through the water sample line;
(E) emitting, by means of said light source, light via the light-transparent flow portion of the water sample line and into the camera;
(F) recording, by means of the electronic control means, said energy supply and the camera, image material of the particle content in said partial flow in the water sample line; and
(G) transmitting, by means of the electronic control means and said energy supply, this image material to the remote data receiving means. Thereby, image material being transmitted from the image analysis apparatus may be monitored online at a remote site.

According to a first embodiment of the method, said electronic control means may also be structured for processing of image material from the camera. As an alternative or addition, said data receiving means may also be structured for processing of image material from the camera.

Further, the inlet and an outlet of the water sample line may be connected to the underwater line at a connection site located in vicinity of the injection well, for example within 500 m of the injection well. For example, the connection site may be comprised of a wellhead for the injection well.

Yet further, the injection water may be shipped out from a surface installation, for example a surface installation located offshore, including a bottom-fixed platform, a floating installation or a floating vessel. As an alternative or addition, injection water taken from a body of water within which the underwater line is located, for example seawater, may be shipped out. As a further alternative or addition, injection water comprising produced water from a separation plant for hydrocarbon fluid, the plant of which is connected to the surface installation, may be shipped out.

Further, said data receiving means may be disposed on said surface installation, such as described above in context of the present technical system.

As an alternative or addition, the injection water may be shipped out from at least one underwater installation for treatment of the injection water. This injection water may be taken from a body of water within which the underwater installation is located, for example seawater, and/or the injection water may comprise produced water from a separation plant for hydrocarbon fluid, the plant of which is connected to said underwater installation. Also in this context, said data receiving means may be disposed on a surface installation, for example on a bottom-fixed platform, a floating installation or a floating vessel. Alternatively, the data receiving means may be disposed at a site onshore, for example in a building within which an operator of said underwater installation is located.

Said at least one underwater installation may comprise at least one device for filtering solid particles from the injection water, and/or at least one device for removal, without filtration, of solid particles from the injection water, and/or at least one device for chemical treatment of the injection water, such as described above.

Yet further, the image material from the camera may be transmitted to the remote data receiving means via a cabled data communication link, or via a wireless data communication link, for example a radio frequency connection or an acoustic connection.

According to a third aspect of the invention, a use of a technical system according to the first aspect of the invention is provided for online measuring and monitoring of the particle content in an injection water flow in an underwater line.

According to a fourth aspect of the invention, a use of method according to the second aspect of the invention is provided for online measuring and monitoring of the particle content in an injection water flow in an underwater line

SHORT DESCRIPTION OF FIGURES OF THE EXEMPLARY EMBODIMENTS

Hereinafter, some non-limiting examples of preferred embodiments of the invention are described, where.

The figures are very schematic and only show details and equipment essential to the understanding of the invention. For the sake of simplicity, FIGS. 2-4 do not show any pumping means for pumping injection water through the underwater pipeline. Further, the figures are much distorted with respect to relative dimensions of details and equipment, which are also depicted with a very simplified shape and richness of detail.

SPECIFIC DESCRIPTION OF THE EXEMPLARY EMBODIMENTS

Figure 1:
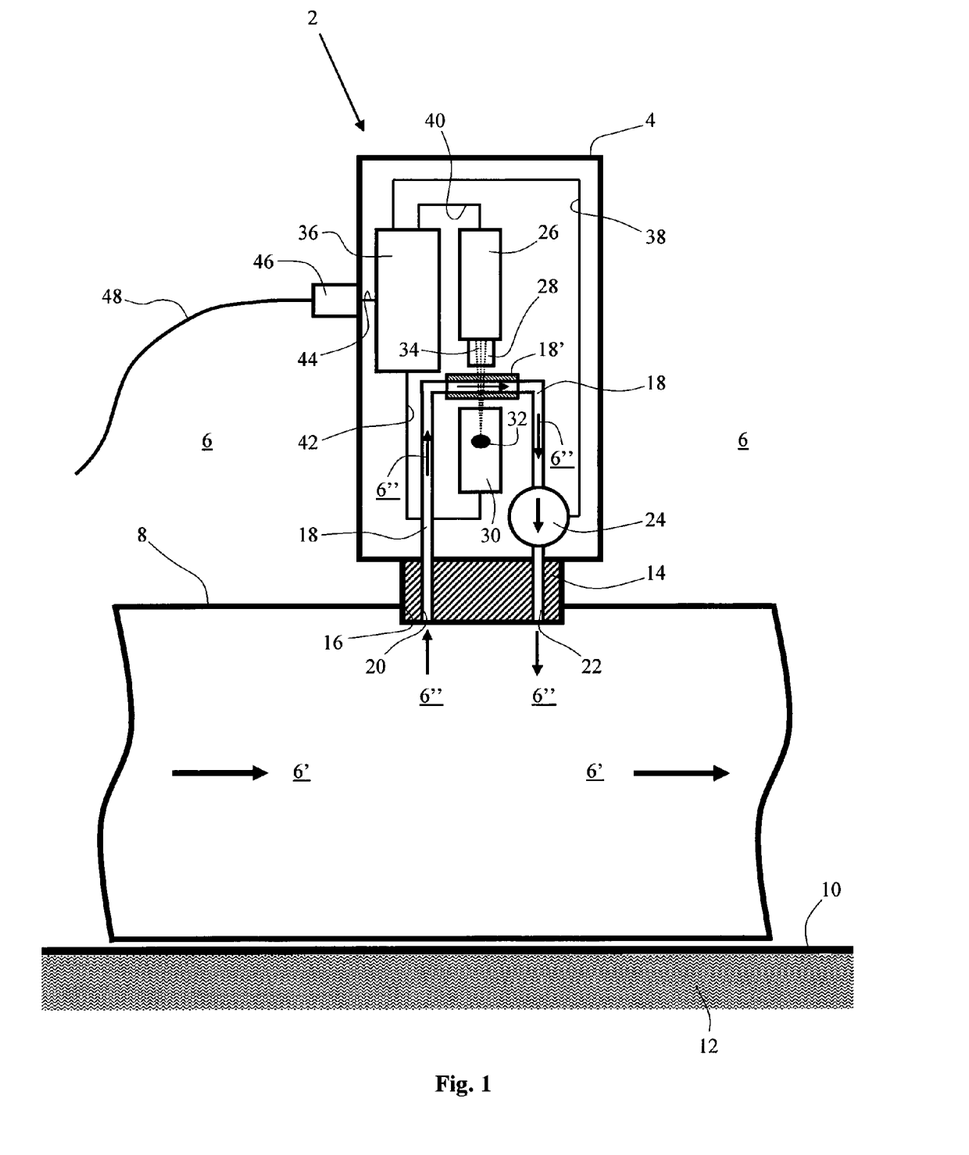
FIG. 1 shows, very schematically, an example of an image analysis apparatus constituting a part of a technical system according to the invention, wherein the image analysis apparatus is shown connected, in a flow-communicating manner, to a portion of an underwater pipeline transporting injection water containing various inorganic and organic particles.

FIG. 1 shows one embodiment of an image analysis apparatus 2 constituting a part of a technical system according to the invention. The image analysis apparatus 2 is disposed in a water-tight housing 4 placed under water within seawater 6. Further, the image analysis apparatus 2 is connected, in a flow-communicating manner, to an underwater pipeline 8 containing a flow of injection water 6', the pipeline of which is placed on a seabed 10 above a subsurface 12. The flow direction of the injection water 6' is depicted with bold, black arrows in the pipeline 8. The water-tight housing 4 is connected to the pipeline 8 via a connection stub 14 fixed, in a sealing manner, in a through side opening 16 in the pipeline 8.

Among other things, the image analysis apparatus 2 comprises a water sample pipe 18 provided with an inlet 20 and an outlet 22 for throughput of a partial flow 6" of the injection water flow 6'. The flow direction of the partial flow 6" is depicted with thin, black arrows within and beside the water sample pipe 18. A light-transparent flow portion 18' is also disposed along the water sample pipe 18. Further, a pump 24 is connected, in a flow-communicating manner, to the water sample pipe 18 for transport of the partial flow 6". The pump 24 is structured so as to be reversible and hence is structured in a manner allowing it to reverse the flow direction of the partial flow 6" through the water sample pipe 18 for cleaning thereof. Such a reverse flow may contribute to disengage and remove a potential particle blockage in the water sample pipe 18. Further, a so-called CCD-camera 26 with a microscope lens 28 is disposed at a first side of the light-transparent flow portion 18'. A light source 30 provided with light-diodes 32 (LED-lighting) is disposed at a second side, opposite the first side, of the light-transparent flow portion 18' of the water sample pipe 18 for emission of visible light 34 through the flow portion 18' and into the camera 26 for recording image material of the particle content in the partial flow 6". Moreover, the image analysis apparatus 2 comprises an electronic data processing unit 36 which, in this context, is structured for (a) control of the image recording of the camera 26; (b) reception and processing of image material from the camera 26; and (c) transmission of processed image material to a remote data receiving means for online monitoring and verification of the particle content in the partial flow 6", and hence of the particle content in the injection water flow 6' in the underwater pipeline 8. In this embodiment, the data processing unit 36 is also structured for control of the pump 24. For these reasons, the data processing unit 36 is connected to lines 38, 40, 42 and 44, the opposite ends of which are connected, respectively, to the pump 24, the camera 26, the light source 30 and an underwater connector 46 disposed on the outside of the water-tight housing 4. The line 44 is connected to the connector 46 via a water-tight bushing (not shown) in the housing 4. On its opposite side, the connector 46 is connected to a data communication cable 48 for transmission of processed image material from the data processing unit 36 and further onto said remote data receiving means. The very processing and image analysis of the raw image material received from the camera 26 is not discussed in further detail herein given that such processing and image analysis is considered to be prior art from, for example, the above-mentioned patent publication WO 00/46586 (which corresponds to U.S. Pat. No. 7,162,057). In this embodiment, the operation of the pump 24, the light source 30, the camera 26 and the data processing unit 36 is carried out by means of energy supplied from an energy source located at a distance from the image analysis apparatus 2, the energy source of which is cable-connected, in this context, to the image analysis apparatus 2 via the data communication cable 48.

Three different embodiments of a technical system according to the invention will be shown now. All embodiments make use of the above-mentioned image analysis apparatus 2 and data communication cable 48 for transmission of processed image material from the data processing unit 36 and further onto a remote data receiving means.

Figure 2:
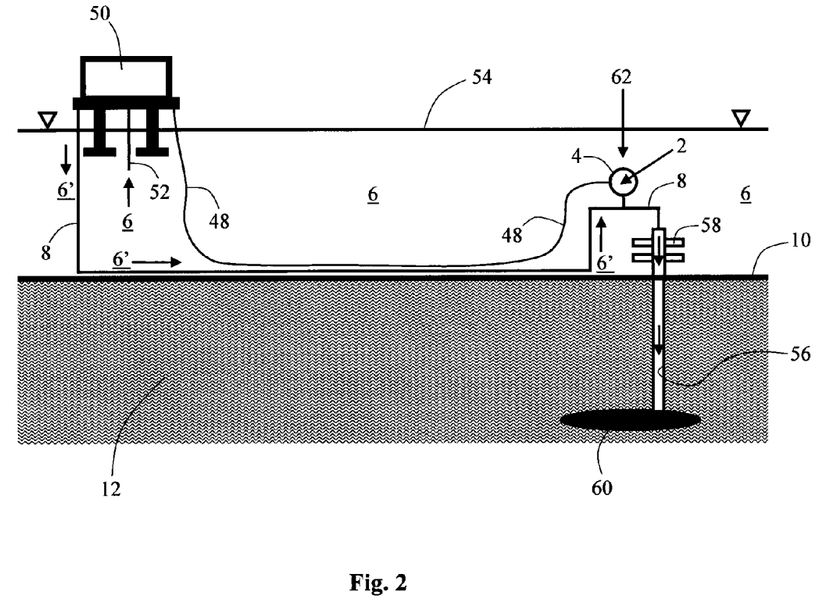
FIG. 2 shows a first embodiment of a technical system according to the invention, wherein injection water is pumped from a floating surface installation offshore and down into a remote injection well via an underwater pipeline, whereas image material of particles in the injection water is transmitted to the installation via a data communication cable, and from an underwater image analysis apparatus associated with the underwater pipeline.

FIG. 2 shows a first embodiment of the present technical system. In this first embodiment, untreated seawater 6 is pumped up to a floating surface installation 50 offshore for conventional particle filtration and chemical treatment of the seawater 6. Via an inlet pipe 52 connected to the surface installation 50, the seawater 6 is pumped up from a water layer located immediately below the surface 54 of the sea. After said water treatments on the surface installation 50, treated injection water 6' is pumped to a remote injection well 56 on the seabed 10 via the underwater pipeline 8 and a wellhead 58 connected to the well 56. Then, the injection water 6' is pumped down and into a subterranean oil reservoir 60 in the subsurface 12 for secondary recovery of crude oil therefrom. The flow direction of the injection water 6' is depicted with black arrows in FIG. 2. This flow pattern is identical in all three embodiments of the present technical system. In this context, the water sample pipe 18, i.e. the inlet 20 and the outlet 22 therein, of the image analysis apparatus 2 is connected, in a flow-communicating manner, to the pipeline 8 at a connection site 62, the site of which is located, in this context, in the immediate vicinity of the injection well 56. In another embodiment variant (not shown), this connection site may be comprised of said wellhead 58 for the injection well 56. Thereby, the image analysis apparatus 2 may be connected to, or integrated in, the wellhead 58. In this first embodiment, the data receiving means of the technical system is located on the floating surface installation 50, the installation of which also is a shipment site for the injection water 6'. Thereby, the electronic data processing unit 36 in the image analysis apparatus 2 may transmit, in a continuous manner via said data communication cable 48, processed image material of the particle content of the injection water 6' to the data receiving means on the surface installation 50. By so doing, it is also possible to carry out online measuring, monitoring and verification of this particle content on the shipment site for the injection water 6', i.e. on the floating surface installation 50. This is very practical with respect to being able to quickly initiate remedial actions should the particle content in the injection water flow 6' exhibit a negative development.

Figure 3:
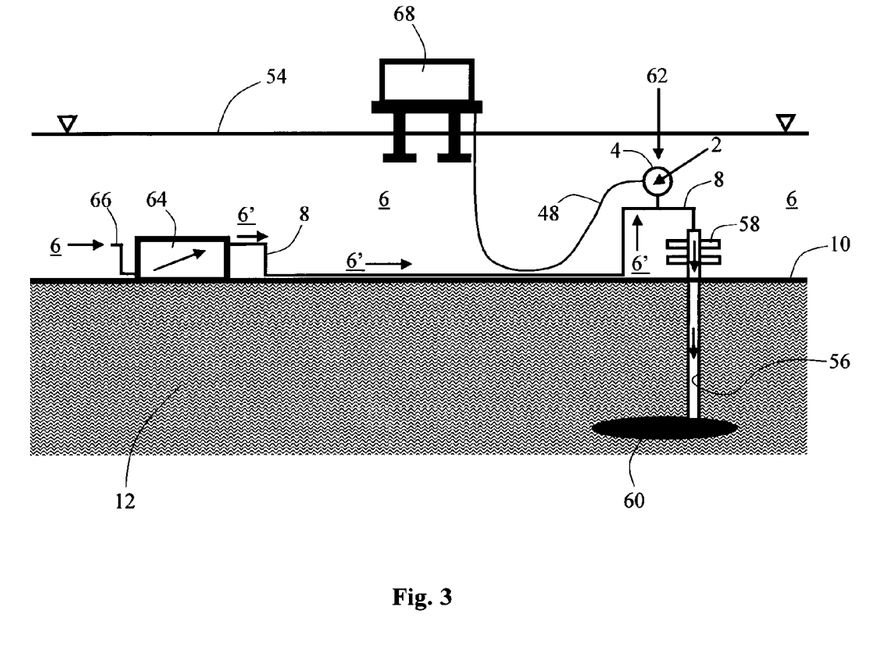
FIG. 3 shows a second embodiment of a technical system according to the invention, wherein injection water is pumped from an underwater installation and down into a remote injection well via an underwater pipeline, whereas image material of particles in the injection water is transmitted to a remote and floating surface installation offshore via a data communication cable, and from an underwater image analysis apparatus associated with the underwater pipeline.

Reference is now made to FIG. 3, which shows a second embodiment of the present technical system. In this second embodiment, untreated seawater 6 is conducted into an underwater installation 64 for various treatment of the seawater 6. The seawater 6, which surrounds the underwater installation 64, is taken from a water layer located immediately above the seabed 10 and is conducted into the underwater installation 64 via an inlet pipe 66 connected thereto. This underwater installation 64 comprises, among other things, at least one device (not shown) for removal, without filtration, of solid particles from the seawater 6. An example of such an underwater device is described in said WO 2007/035106 A1, wherein solid particles are precipitated from the seawater 6 by means of gravitation, so-called sedimentation. Furthermore, the underwater installation 64 comprises at least one device (not shown) for chemical treatment of the water emanating from the first-mentioned device for sedimentation of solid particles. This emanating water is brought into contact with at least one type of water-soluble solid-state chemical for gradual dissolution and mixing with the water. Such water-soluble solid-state chemicals may comprise chlorine, biocide, oxygen scavengers, corrosion inhibitors and/or scale inhibitors. An example of such a chemical treatment device is described in the above-mentioned WO 2004/090284 A1. In this embodiment, the underwater installation 64 is comprised of a shipment site for the injection water 6'. After said water treatments in the underwater installation 64, treated injection water 6' is pumped through an underwater pipeline 8 connected to said remote wellhead 58, which again is connected to the injection well 56 and the oil reservoir 60. Also in this case, the flow direction of the injection water 6' is depicted with black arrows in FIG. 3. In this second embodiment, the data receiving means of the technical system is located on a separate, floating surface installation 68. This separate surface installation 68 is not a shipment site for the injection water 6', but it may, for example, be an installation associated with recovery from, or injection into, another oil reservoir within the same geographic area. Thereby, the data processing unit 36 of the image analysis apparatus 2 may transmit, in a continuous manner via said data communication cable 48, processed image material of the particle content in the injection water 6' to a data receiving means placed on the separate surface installation 68. By so doing, it is also possible to carry out online measuring, monitoring and verification of the particle content on the surface installation 68.

Figure 4:
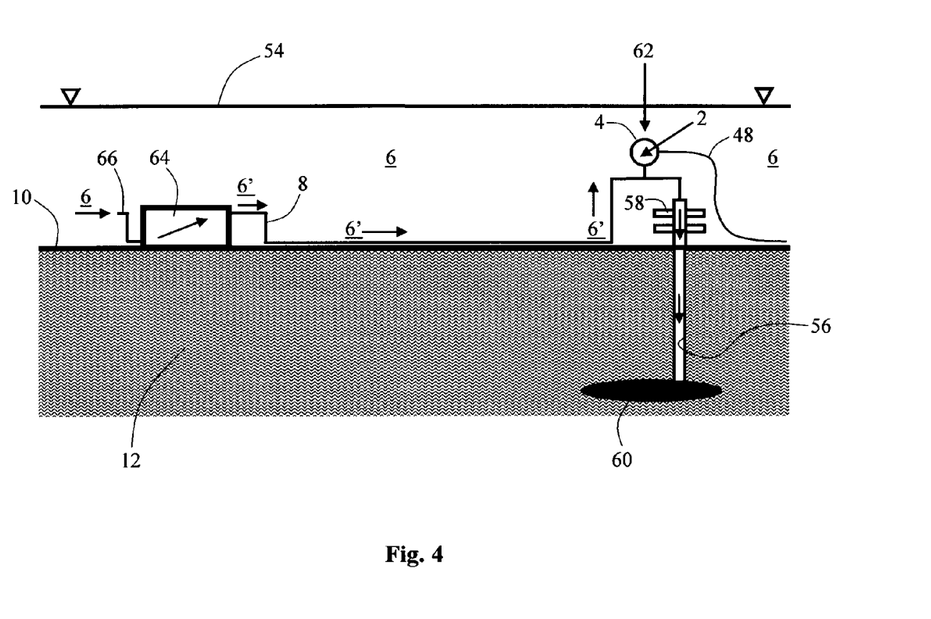
FIG. 4 shows a third embodiment of a technical system according to the invention, wherein injection water is pumped from an underwater installation and down into a remote injection well via an underwater pipeline, whereas image material of particles in the injection water is transmitted to a remote site onshore via a data communication cable, and from an underwater image analysis apparatus associated with the underwater pipeline.

Reference is now made to FIG. 4, which shows a third embodiment of the present technical system. This embodiment is substantially equal to the preceding embodiment according to FIG. 3, however with the difference that the data communication cable 48 is connected, in this context, to a remote site onshore (not shown). Thereby, the data processing unit 36 of the image analysis apparatus 2 may transmit, in a continuous manner, processed image material of said particle content to a data receiving means placed at the remote site onshore. By so doing, it is also possible to carry out online measuring, monitoring and verification of the particle content at the remote site onshore.

The invention claimed is:

1. A technical system for online measuring and monitoring of the particle content in a flow of injection water, wherein the technical system comprises:
   a subsea injection well configured to inject the injection water into a subterranean reservoir;
   an underwater line extending from a shipment site to the injection well, wherein the underwater line is configured to transport the injection water to the subsea injection well;
   a data gathering means comprising an image analysis apparatus;
   a data receiving means located at a distance from the image analysis apparatus and communicatively coupled to the image analysis apparatus with a data communication link;
   wherein the image analysis apparatus is disposed under water and comprises:
      a water sample line including an inlet and an outlet coupled to the underwater line at a connection site located between the shipment site and the injection well, wherein the connection site is upstream of the injection well and within 500 m of the injection well, wherein the inlet and the outlet of the water sample line are in fluid communication with the underwater line and the injection water therein, and wherein the water sample line is configured to receive a portion of the injection water in the underwater line;
      at least one pumping means connected, in a flow-communicating manner, to the water sample line for transport of the portion of the injection water from the underwater line through the water sample line;
      at least one light-transparent flow portion disposed along the water sample line;
      at least one camera for recording image material of the particle content in the partial flow, wherein the camera is disposed at a first side of the light-transparent flow portion;
      at least one light source for emission of light via the light-transparent flow portion and into the camera;
      at least one electronic control means configured to (a) control of the image recording of the camera; (b) receive the image material from the camera; and (c) transmit the image material from the data gathering means to said data receiving means; and
      at least one energy supply for operation of said pumping means, light source, camera and electronic control means;
      wherein the electronic control means of the image analysis apparatus is connected to the data receiving means, whereby the image material being transmitted from the image analysis apparatus may be monitored online at a remote site,
      wherein the water sample line, pumping means, light-transparent flow portion, camera, light source and electronic control means of the image analysis apparatus are disposed in a water-tight housing disposed under water.

2. The technical system according to claim 1, wherein said pumping means is configured to reverse the flow direction of the portion of the injection water through the water sample line for cleaning of the water sample line.

3. The technical system according to claim 1, wherein said camera comprises a CCD-camera.

4. The technical system according to claim 1, wherein said light source comprises at least one light source disposed at a second side, opposite the first side, of the light-transparent flow portion of the water sample line for emission of light therethrough and into the camera for recording image material of the particle content in the partial flow.

5. The technical system according to claim 1, wherein said electronic control means is configured to process the image material from the camera.

6. The technical system according to claim 1, wherein said data receiving means is configured to process the image material from the camera.

7. The technical system according to claim 1, wherein the image analysis apparatus includes at least two water sample lines, including at least one primary water sample line and at least one secondary water sample line;
   wherein each of the at least two water sample lines is provided with its own camera; and
   wherein the image analysis apparatus includes a valve means for selective control of the partial flow into a selected water sample line.

8. The technical system according to claim 1, wherein said shipment site for the injection water comprises a surface installation.

9. The technical system according to claim 8, wherein the injection water comprises water taken from a body of water within which the underwater line is located.

10. The technical system according to claim 1, wherein said shipment site for the injection water comprises at least one underwater installation for treatment of the injection water.

11. The technical system according to claim 10, wherein the injection water comprises water taken from a body of water within which the underwater installation is located.

12. The technical system according to claim 10, wherein said underwater installation comprises at least one device for removal, without filtration, of solid particles from the injection water.

13. The technical system according to claim 10, wherein the underwater installation comprises at least one device for chemical treatment of the injection water.

14. The technical system according to claim 10, wherein the underwater installation comprises at least one device for destruction of organic material in the injection water.

15. A method for online measuring and monitoring of the particle content in a flow of injection water, wherein the method makes use of a technical system comprising a data gathering means, a data communication link and a data receiving means, and wherein the data gathering means includes an image analysis apparatus comprising:
   at least one water sample line including an inlet and an outlet;

at least one pumping means connected, in a flow-communicating manner, to the water sample line;

at least one light-transparent flow portion disposed along the water sample line;

at least one camera disposed at a side of the light-transparent flow portion;

at least one light source disposed at the light-transparent flow portion of the water sample line;

at least one electronic control means configured to (a) control of the image recording of the camera; (b) receive the image material from the camera; and (c) transmit image material to said data receiving means; and at least one energy supply for operation of said pumping means, light source, camera and electronic control means, wherein the method comprises using a technical system that also comprises an underwater line for containing said injection water flow;

wherein the method also comprises:

(A) disposing at least said water sample line, pumping means, light-transparent flow portion, camera, light source and electronic control means of the image analysis apparatus in a water-tight housing and placing the housing under water;

(B) flowing the injection water through the underwater line from a shipment site to a subsea injection well;

(C) injecting the injection water into a subterranean reservoir with the injection well;

(D) connecting, in a flow-communicating manner, the inlet and the outlet of the water sample line to the underwater line at a connection site located between the shipment site and the injection well, wherein the connection site is upstream of the injection well and within 500 m of the injection well;

(E) connecting the image analysis apparatus to the data receiving means located at a distance from the image analysis apparatus with said data communication link;

(F) transporting a partial flow of the injection water flow through the water sample line with said pumping means;

(G) emitting light with the light source through the light-transparent flow portion of the water sample line and into the camera;

(H) recording the image material of the particle content in said partial flow in the water sample line using the electronic control means, said energy supply and the camera; and (I) transmitting the image material to the remote data receiving means;

(J) using the image material transmitted from the image analysis apparatus to the remote data receiving means at a remote site to monitor the particle content in the injection water flow;

(K) initiating a remedial action in response to a change in the particle content in the injection water flow monitored at the remote site.

16. A system for online measuring and monitoring of a particle content in a flow of injection water, the system comprising:

a subsea injection well configured to inject the injection water into a subterranean reservoir;

a pipeline extending from a shipment site to the subsea injection well, wherein the pipeline is configured to transport the injection water from the shipment site to the underwater injection well;

an image analysis apparatus disposed underwater and coupled to the pipeline at a connection site located between the shipment site and the injection well, wherein the connection site is upstream of the injection well and within 500 m of the injection well, wherein the image analysis apparatus comprises:

a water sample line including an inlet in fluid communication with the underwater pipeline and an outlet in fluid communication with the underwater pipeline, wherein the water sample line is configured to flow a portion of the injection water through the image analysis apparatus;

a light-transparent flow portion disposed along the water sample line;

a camera disposed adjacent the light-transparent flow portion and configured to record image material of the particle content in the portion of the injection water flowing through the water sample line;

a light source configured to emit light through the light-transparent flow portion and into the camera;

a data processing unit configured to receive the image material from the camera and communicate the image material to a remote location.

17. The system of claim 16, wherein the data processing unit is configured to transmit the image material to a data receiving means at the remote location for monitoring the particle content.

18. The system of claim 16, wherein the particle content comprises a type, an amount, or a size of the particles in the portion of the injection water flowing through the water sample line.

19. The system of claim 16, wherein the image analysis apparatus is mounted to the pipeline with a connection stub disposed in a side opening of the pipeline, wherein the inlet of the water sample line and the outlet of the water sample line extend through the connection stub.

* * * * *